United States Patent

Kellner et al.

[11] Patent Number: 6,042,815
[45] Date of Patent: Mar. 28, 2000

[54] WATER AND OIL EMULSION SOLID COSMETIC COMPOSITION

[75] Inventors: David Martin Kellner, Hollis, N.Y.; Julio Gans Russ, Westfield; Ida Marie Sandewicz, Spotswood, both of N.J.; Robin Felice Shandler, Commack, N.Y.; Tian Xiang Wang, Edison, N.J.

[73] Assignee: Revlon Consumer Products Corporation, New York, N.Y.

[21] Appl. No.: 09/175,941

[22] Filed: Oct. 21, 1998

[51] Int. Cl.[7] ............. A61K 7/021; A61K 7/42; A61K 7/025; A61K 7/32; A61K 7/00
[52] U.S. Cl. ............. 424/63; 424/59; 424/64; 424/65; 424/400; 424/401; 514/844; 514/937; 514/944
[58] Field of Search ............. 424/400, 401, 424/59, 63, 64, 65; 514/844, 937, 944

[56] References Cited

U.S. PATENT DOCUMENTS

| | | | |
|---|---|---|---|
| 4,087,555 | 5/1978 | Barnett | 424/357 |
| 4,226,889 | 10/1980 | Yuhas | 424/59 |
| 4,322,400 | 3/1982 | Yuhas | 424/59 |
| 4,507,279 | 3/1985 | Okuyama | 424/63 |
| 4,822,602 | 4/1989 | Sabatelli | 424/65 |
| 4,923,478 | 5/1990 | Naggiar | 424/70 |
| 5,462,736 | 10/1995 | Rech et al. | 424/401 |
| 5,552,136 | 9/1996 | Motley | 424/68 |
| 5,591,473 | 1/1997 | McArdle | 426/573 |
| 5,597,849 | 1/1997 | McGinity et al. | 514/648 |
| 5,645,903 | 7/1997 | Tanaka et al. | 428/34.1 |
| 5,688,831 | 11/1997 | El-Nokaly | 514/938 |
| 5,753,243 | 5/1998 | Cunningham | 424/401 |
| 5,928,655 | 7/1999 | Avalle | 424/401 |

FOREIGN PATENT DOCUMENTS

| | | |
|---|---|---|
| 10101703 | 4/1998 | Japan . |
| 9531967 | 11/1995 | WIPO . |

*Primary Examiner*—Shelley A. Dodson
*Assistant Examiner*—Marina Lamm
*Attorney, Agent, or Firm*—Julie Blackburn

[57] ABSTRACT

A water and oil emulsion solid cosmetic composition comprising 0.1–20% of a primary soap based gelling agent, 0.01–20% of a secondary gelling agent selected from the group consisting of an aqueous phase gelling agent, an oil phase gelling agent; and mixtures thereof, 0.1–30% emollient oil, 0.1–20% surfactant, 0.1–50% particulates having a particle size of 0.5 to 100 microns, and 5–95% water. The composition is moisturizing, provides a cool feel on application, and a smooth finish on the skin.

21 Claims, No Drawings

6,042,815

WATER AND OIL EMULSION SOLID COSMETIC COMPOSITION

TECHNICAL FIELD

The invention is in the field of solid cosmetic compositions for application to skin and lips.

BACKGROUND OF THE INVENTION

Cosmetic compositions such as make-up, blush, lipstick, eyeshadow, and concealer are often sold in the form of sticks or solids. Sticks are advantageous because they can be applied directly to the skin, removing the need for applicators. Solids are often dispensed from various types of compacts. While the latter often require applicators, their solid form prevents them from dripping and leaking. Most often, solids in the form of sticks are anhydrous, and require significant amounts of wax or powder to form the stick structure. This, in turn, causes certain undesireable properties. For example, sticks containing large amounts of powder tend to be very brittle and easily broken, and the film applied to the skin or lips may feel dry. Sticks which contain appreciable levels of wax may have undesireable payoff characteristics, and the film applied to skin or lips may feel too heavy and greasy. Inclusion of water in the stick composition would help to combat the undesireable effects, however most of the ingredients which are necessary to formulate aethestically pleasing cosmetic sticks are not compatible with water. Thus, it has been difficult to formulate pigmented cosmetic sticks or solids which contain significant amounts of water and yet still exhibit commercially acceptable properties. Such water-containing sticks have been traditionally very unstable. Accordingly, there is a need for stable, pigmented cosmetic sticks and solids containing appreciable levels of water.

It is an object of the invention to formulate solid cosmetic compositions which provide a cooling feel to the skin, a smooth texture finish when applied to the skin.

It is an object of the invention to formulate solid or stick cosmetic compositions which are capable of moisturizing the skin.

It is an object of the invention to formulate stable, pigmented cosmetic sticks which contain appreciable amounts of water.

It is an object of the invention to formulate stable, pigmented cosmetic sticks in the emulsion form, i.e. water-in-oil or oil-in-water.

It is an object of the invention to provide a stable make-up stick or solid for application to skin as a foundation.

It is an object of the invention to provide stable, pigmented cosmetic sticks or solids for application as blush, eyeshadow, concealer, lipstick, and the like.

SUMMARY OF THE INVENTION

The invention is directed to a water and oil emulsion solid cosmetic composition comprising, by weight of the total composition:

0.1–20% of a carboxylated salt gelling agent,
0.01–20% of a secondary gelling agent selected from the group consisting of:
  (a) an aqueous phase gelling agent,
  (b) a oil phase gelling agent; and
  (c) mixtures thereof,
0.1–30% emollient oil,
0.1–20% surfactant,
0.1–50% particulates having a particle size of 0.5 to 100 microns, and
5–95% water.

DETAILED DESCRIPTION

All percentages mentioned herein are percentages by weight unless otherwise indicated. The term "solid" means that the cosmetic stick compositions are solid or semi-solid at room temperature, i.e. 25° C. The compositions may also be in the form of a stick. The term "stick" refers to cosmetic compositions having a consistency such that they can be molded into the form of a stick—for instance by being heated until molten and then poured into a mold and cooled. Also included within the definition of "stick" are anhydrous compositions of the invention that are capable of being formed into sticks, but are poured into pans or other types of cake or cream forms to deliver certain consumer benefits. For example, an eyeshadow composition in accordance with the invention may be molded in the stick form, but it may be desired to pour it into a pan because this container is more desireable from a consumer standpoint.

I. Primary Carboxylated Salt Gelling Agent

The cosmetic stick compositions of the invention comprise 0.1–20%, preferably 0.5–15%, more preferably 1–10% of a primary gelling agent which is a carboxylated salt gelling agent. The term "carboxylated salt gelling agent" means the gelling agent is formed by the reaction of a salt with a compound containing at least one carboxylic acid group. Preferably the carboxylic acid-containing compound is a fatty acid and the carboxylated salt gelling agent is the salt of a water insoluble fatty acid and a base. While the fatty acid used to make the carboxylated salt gelling agent is generally water insoluble, the resulting gelling agent may be water soluble or water insoluble. Preferably, the carboxylated salt gelling agent in accordance with this invention is water soluble, i.e. after the water insoluble fatty acid is reacted with the metallic cation (such as sodium) the gelling agent is water soluble. Suitable fatty acids used to make the gelling agent are $C_{12-40}$ straight or branched chain, saturated or unsaturated fatty acids. Suitable fatty acids include lauric, myristic, palmitic, stearic, oleic, linoleic, linolenic, behenic, caprylic, stearic, and so on. In addition, oils containing fatty acid mixtures, such as palm kernel, olive, tallow, peanut, rapeseed, and the like may be used as the fatty acid component. Preferred are $C_{16-22}$ fatty acids such as lauric, stearic, or behenic. Most preferred is where the fatty acid is stearic acid.

A variety of cations may be used. Generally the type of cation selected will determine whether the resulting gelling agent is water soluble or water insoluble. Generally cations such as sodium, potassium, or low molecular weight amines or alkanolamines will provide water soluble gelling agents. Suitable amines are ammonia and derivatives thereof. Suitable alkanolamines include mono- di- and triethanolamines.

Examples of gelling agents which may be used in the compositions of the invention are sodium, potassium, aluminum, magnesium, or calcium salts of stearic, behenic, caprylic, tallowic, tallic, cocoic, or lauric acids, and so on. Preferably the gelling agent used in the compositions of the invention are water soluble salts of fatty acids and sodium, and in particular sodium stearate.

II. The Secondary Gelling Agent

The compositions of the invention comprise 0.01–30%, preferably 0.1–20%, more preferably 0.5–15% of a secondary gelling agent which is an aqueous phase gelling agent, an oil phase gelling agent, or mixtures thereof. Preferably the compositions of the invention contain both an aqueous phase gelling agent and an oil phase gelling agent, which will provide optimal long term stability.

A. Aqueous Phase Gelling Agent

The term "aqueous phase gelling agent" means an ingredient which is capable of gelling the aqueous phase in the emulsion compositions of the invention. The phrase "capable of gelling the aqueous phase" means the gelling agent, upon mixing with water in a ratio of about 1 to 1 at room temperature (25° C.) is capable of forming either a soft gel having a gel having a viscosity of about 1,000 to 800,000 centipoise at 25° C., and/or a gel strength of about 10 to 5,000 grams/cm$^2$ at 25° C. as measured using a TA.XT2i texture analyzer with a ½ inch diameter cylindrical probe. In order to be an adequate aqueous phase gelling agent, the ingredient is preferably water soluble, and may be either nonionic or anionic in character. A variety of gelling agents are suitable for gelling the aqueous phase, including polysaccharides, PPC's, acrylic polymers, and the like.

(1) Polysaccharides

Polysaccharides are suitable aqueous phase gelling agents. Examples of polysaccharides include galactans, galactomannans, glucomannans, polyuronic acids, and the like. Preferably the polysaccharides exhibit pendant hydrophilic groups, which are preferably sulfate. Suitable galactans are agar, agarose, kappa carageenan, iota carageenan, lambda carageenan, and the like. Examples of suitable galactomannans are locust bean gum and guar; examples of glucans are cellulose, starch, dextrans, pullulan, beta 1,3-glucans, chitin, xanthan, tamarind and the like; examples of glucomannans are konjac; examples of polyuronic acids are algin, alginates, pectins; examples of heteropolysaccharides are gellan, welan, gum arabic, karaya gum, okra gum, aloe gum, gum tragacanth, gum ghatti quinceseed gum, psyllium, starch arabinogalactan and so on. Also suitable are dextran sulfate, heparin, pectin, sodium alginate, cellulose gum, cellulose acetate priopionate carboxylate, hydroxyethyl cellulose, hydroxypropyl cellulose, and the like, and mixtures thereof. The polysaccharides may be derivatized with various groups such as sulfate, carboxylate, hydroxyl, and so on, provided the resulting polysaccharide still retains water solubility, or at the very least water dispersibility.

Preferred are galactans, particularly galactans where the pendant hydrophilic groups are sulfate groups. Most preferred is agar and carageenan, which are anionic polysaccharides comprised of basic repeating units of 1,3-linked beta-D-galactopyranose and 1,4-linked 3,6-anhydro-alpha-L-galactopyranose saccharide moieties and having pendant sulfate groups. These galactans may be further modified as taught in Aoki, T. T.; Araki & M. Kitamikado; 1990, Vibrio sp. AP-2. *Eur. J. Biochem*, 187, 461–465, which is hereby incorporated by reference, provided it contains the requisite number of hydrophilic pendant groups. The average molecular weight of agar ranges between 35,700 and 144,000 daltons. The galactans suitable for use in the compositions of the invention may be from any suitable source or locale. For example an article authored by M. Lahaye and C. Rochas, *Hydrobiologia*, 221, 137–148, 1991, which is hereby incorporated by reference, discusses the numerous different types of galactans from different origins of seaweed species, all of which are suitable for use in the compositions of the invention. Also suitable for use in the compositions of the invention are chemically modified galactans, such as those taught in an article authored by K. B. Guiseley in *Industrial Polysaccharides: Genetic Engineering. Structure/Property Relations and Applications*, Edited by M. Yalpani, 1987, Elsevier Science Publishers, which is hereby incorporated by reference. The Guiseley article teaches methods for the chemical modification of agar to obtain optimum gelling properties. In general, any modification of the galactans which does not affect the helical conformation (i.e. which is obtained via linkage of the O6 and O4 of galactose to the O2 of 3,6-anhydrogalactose) will preserve the gelling capability and is suitable for use in the compositions of the invention provided the requisite number of hydrophilic groups are present. The hydrophilic groups provide a polysaccharide which is water soluble.

(2) Protein/Polysaccharide Complexes ("PPC")

Also suitable for use as the aqueous phase gelling agent are PPC's formed by the reaction of the anionic polysaccharides mentioned above and a protein. The term "protein" when used in accordance with this invention means a peptide chain having at least two amino acid residues, preferably at least five, and more preferably more than one hundred amino acid residues. Most preferably the protein is a high molecular weight polypeptide which is preferably water soluble, and may be natural, plant (vegetable) proteins, or animal derived proteins, as well as synthetic proteins provided they react with the hydrophilic pendant groups on the polysaccharide to form a PPC. The isoelectric point of the protein used to make the PPC is not critical. Examples of natural proteins include albumen, amylase, amyloglucosidase, arginine/lysine polypeptide, casein, catalase, collagen, crystalline, cytochrome C, deoxyribonuclease, elastin, fibronectin, gelatin, gliadin, glucose oxidase, glycoproteins, hexyldecyl ester of hydrolyzed collagen, human placental protein, human placental enzymes, iodized corn protein, keratin, lactoferrin, lactoglobulin, lactoperoxidase, lipase, milk protein, hyristoyl glycine/histidine/lysin polypeptide, nisin, oxido reductase, pancreatin, papin, pepsin, placental protein, protease, saccharomyces polypeptides, serum albumin, serum protein, silk, sodium stearoyl lactalbumin, soluble proteoglycan, soybean palmitate, soy, egg, peanut, cottonseed, sunflower, pea, whey, fish, seafood, subtilisin, superoxide dismutase, sutilains, sweet almond protein, urease, wheat germ protein, wheat protein, whey protein, zein, hydrolyzed vegetable protein, and the like. Preferred is casein which is a mixture of phosphoproteins obtained from cow's milk; and milk protein which is a mixture of proteins obtained from cow's milk.

Synthetic proteins or polypeptides may also be suitable. Synthetic proteins may be made by solid phase synthesis, or via recombinant biotechnology proccesses.

Generally, the amino and/or hydroxyl or carboxyl groups found on the protein will react with the pendant hydrophilic groups on the anionic polysaccharide to form a complex, either alone or in the presence of metal ions such as calcium, sodium, magnesium, iron, potassium, and the like, depending on the pH at which the complexation reaction is conducted. For example, if the complexation reaction is conducted above the isoelectric point of the protein used to make the PPC, it is preferable to use a metal ion to facilitate the complexation reaction. On the other hand, if the reaction is conducted at a pH which is at the isoelectric point of the protein used to make the PPC, a metal ion may be desired to facilitate complexation, but is not necessary. Typical reactions are as set forth below:

Complexation Reaction Conducted at pH Above the Isoelectric Point of the Protein Protein

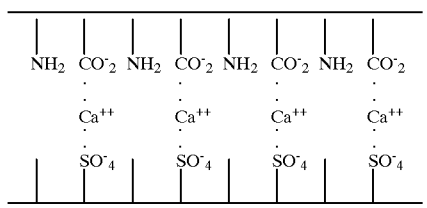

Polysaccharide with pendant sulfate groups

With a typical reaction being:

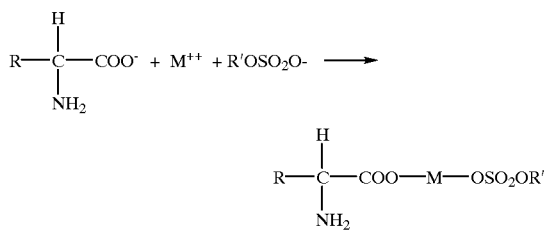

Complexation reaction conducted a pH near the isoelectric point of protein

Protein

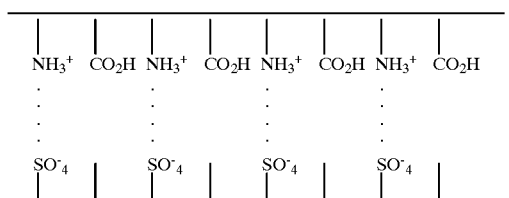

Polysaccharide with pendant sulfate groups

With typical reactions being:

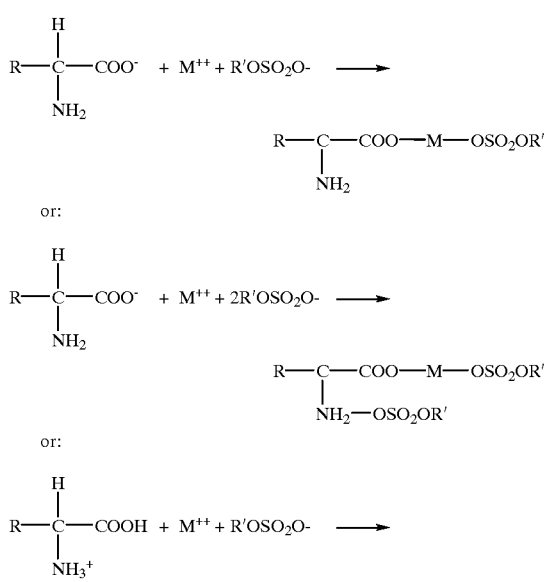

or:

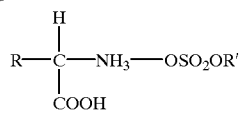

Preferably, the ratio of protein to polysaccharide in the PPC is 1:100 to 100:1, more preferably 1:50 to 50:1, most preferably 1:25 to 25:1. The PPC must contain a net negative charge. For example, when the protein having a net positive charge is reacted with the anionic polysaccharide having a net negative charge, the net negative charge of the polysaccharide is greater than the net positive charge of the protein, thus resulting in a PPC which has a net negative charge. This will ensure that the PPC is water soluble, or at the very least optimally dispersible in water.

The PPC is made by combining appropriate amounts of the protein and polysaccharide in water at temperatures ranging from 25 to 90° C. Some PPC's may form at room temperature depending on the protein and polysaccharide chosen to make the PPC. Suitable ratios are 100 to 1 parts of protein to 1 to 100 parts polysaccharide. The protein polysaccharide complexation reaction should be conducted at a pH which is greater than the isoelectric point of the protein used to make the PPC. If more than one protein is used to make the PPC, it is recommended that the pH be equal to or greater than one or more of the proteins used. Generally, when the complexation reaction is conducted at a pH which is below the isoelectric point of the protein, it is not necessary to add metal ions. However, at this pH, the PPC may form a water insoluble precipitate (also referred to as an M-complex). For example, the isoelectric point of casein is about 4.6. If the complexation reaction of casein with agar is conducted at pH 3.7, an M-complex (i.e. a water insoluble precipitate) is formed. Thus, it is preferred that the complexation reaction occur at a pH which is equal to or greater than the isoelectric point of the protein used to make the PPC. At this pH it may be desireable to add metal ions, such as calcium, potassium, sodium, magnesium, and the like, which will facilitate the complexation reaction. When the complexation reaction is conducted at a pH which is equal to or greater than the isoelectric point of the protein, a T-complex (also known as a water soluble or water dispersible complex) results. While optimally, a T-complex is formed at a pH which is equal to or greater than the isoelectric point of the protein used to form the PPC, after it is formed it is stable and may be incorporated into cosmetic compositions which have a pH which is substantially below the isoelectric point of the protein.

Preferably the cosmetic compositions of the invention contain at least one PPC as the aqueous phase gelling agent, in particular a PPC which is the reaction product of casein or milk protein and agar.

(3) Aqueous Acrylic Polymers

Also suitable as aqueous phase gelling agents are anionic polymers, such as acrylic polymers which are generally sold in the form of aqueous solutions or dispersions. Such acrylic polymers may be homo- or copolymers of monomers such as acrylamide, methacrylamide, acrylic acid, methacrylic acid, $C_{1-22}$ alkyl acrylates, $C_{1-22}$ alkyl methacrylates, and so on. The monomers may also be copolymerized with other organic compounds such as alkoxylated fatty alcohols. The resulting polymers may also be cross-linked with cross-linking agents such as the allyl ether of sucrose, pentaerythritol, or propylene.

Preferred are copolymers of monomers A or B, wherein A is selected from the group consisting of acrylic acid, methacrylic acid, and mixtures thereof; and B is selected from the group consisting of a $C_{1-22}$ alkyl acrylate, a $C_{1-22}$ alky methacrylate, and mixtures thereof Preferably, the A monomer comprises one or more of acrylic acid or methacrylic acid, and the B monomer is selected from the group consisting of a $C_{1-10}$, most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. Most preferably, the acrylic copolymer is supplied in an aqueous solution having a solids content ranging from about 10–60%, preferably 20–50%, more preferably 25–45% by weight of the polymer, with the remainder water. The composition of the acrylic copolymer may contain from about 0.1–99 parts of the A monomer, and about 0.1–99 parts of the B monomer. One example of such an acrylic polymer solution is sold by Seppic, Inc., under the tradename Capigel, in particular, Capigel 98, which is a white liquid having a pH of 2 to 4, a solids content of about 29–31, a density of 1.04 to 1.08, and a viscosity of 700–1000 millipascal seconds at 25° C.

Other types of polymers may contain A and B monomers which are copolymerized with alkoxylated fatty alcohols having the general formula:

$$R-(CH_2CH_2O)_nH$$

wherein n is 1–500.

Examples of polymers containing A and B monomers polymerized with alkoxylated alcohols include acrylates/steareth-50 acrylate copolymer, acrylates/steareth-20 methacrylate copolymer, and the like. Such polymers are sold under the tradenames Acrysol and Acculyn by Rohm & Haas, and Antil by Goldschmidt.

Also suitable are homo- or copolymers of monomers A and B above, which are cross-linked with various cross-linking agents such as the allyl ether of sucrose, the allyl ether of pentaerythritol, or the allyl ether of propylene. Examples of these polymers include those sold under the CTFA name Carbomer, which is defined as a homopolymer of acrylic acid crosslinked with an allyl ether of sucrose, pentaerythritol, or propylene. Carbomers are sold under the tradename Carbopol by B. F. Goodrich or Tego by Goldschmidt, as well as other vendors.

Preferably, the stick compositions of the invention contain an aqueous phase gelling agent which is an anionic polysaccharide or a PPC.

B. Oil Phase Gelling Agent

The cosmetic stick compositions of the invention may contain an oil phase gelling agent, either alone or in combination with an aqueous phase gelling agent. Preferably the cosmetic stick compositions of the invention contain an oil phase gelling agent in addition to an aqueous phase gelling agent. Suitable oil phase gellants are those which capable of gelling, or thickening, the oil phase in the emulsion compositions of the invention. The phrase "capable of gelling the aqueous phase" means the gelling agent, upon mixing with the oil phase in a ratio of about 1 to 1 at room temperature (25° C.) is capable of forming either a soft gel having a gel having a viscosity of about 1,000 to 800,000 centipoise at 25° C., and/or a gel strength of about 10 to 5,000 grams/cm$^2$ at 25° C. as measured using a TA.XT2i texture analyzer with a ½ inch diameter cylindrical probe. The oil phase gelling agents are oil soluble rather than water soluble, and are preferably solids or semi-solids at 25° C. Preferably, they have a melting point ranging from 32 to 100° C. Examples of oil phase gelling agents include fatty alcohols, synthetic waxes, silicone elastomers, oleaginous materials such as lanolin and derivatives, castor oil and derivatives, and the like.

(1) Fatty Alcohols

Fatty alcohols are suitable oil phase gelling agents. Examples of fatty alcohols include $C_{16-22}$ straight or branched chain alcohols such as stearyl alcohol, isostearyl alcohol, cetyl alcohol, cetearyl alcohol, or mixtures thereof.

(2) Silicone Elastomers

Silicone elastomers are also suitable oil phase gelling agents. Elastomers are generally defined as chain polymers having a degree of cross-linking sufficient to provide a rubber-like material. Suitable silicone elastomers are disclosed in U.S. Pat. No. 5,266,321, which is hereby incorporated by references. Other suitable silicone elastomers are disclosed in U.S. Pat. Nos. 4,980,167, and 4,742,142, and 5,599,533, which are hereby incorporated by reference. Preferably the elastomers are at least partially cross-linked, and are the reaction A product of an organopolysiloxane having unsaturated groups such as vinyl or allyl, preferably bonded to another Si atom, and another silicon compound capable of participating in the addition reaction, for example, an organohydrogenpolysiloxane. Silicone elastomers suitable for use are sold by Grant Industries under the Gransil tradename, GE Silicones, and Dow Corning Corporation.

(3) Synthetic Waxes

Synthetic waxes are also suitable oil phase gelling agents. Preferred synthetic waxes are ethylene homo- or ethylene copolymers. The molecular weight of the ethylene homopolymer and/or copolymers used as the wax component may vary, so long as the melting point of the homo- or copolymer either alone or in combination is not greater than 135° C. Generally polyethylene waxes having a melting point range of 30 to 135° C. will have a molecular weight ranging from about 100 and 2,000. Preferably the ethylene copolymers are comprised of ethylene monomer units in either repetitive or randon sequence, in combination with monomer units of the following formula:

$$CH_2=CH-R_1$$

wherein $R_1$ is a $C_{1-30}$ straight or branched chain saturated or unsaturated alkyl, aryl, or aralkyl, preferably a $C_{1-10}$ straight or branched chain alkyl. Examples of ethylene homo- and copolymers which may be used in the invention are set forth in U.S. Pat. No. 5,556,613, which is hereby incorporated by reference.

(4) FattyAcids

Also suitable as oil phase gelling agents are fatty acids or hydroxy-fatty acids. Suitable fatty acids have 12–22 carbon atoms, and may be substituted with one or more hydroxyl groups in the carbon backbone. Preferred are hydroxyl subsituted fatty acids such as 12-hydroxystearic acid.

(5) Hydrocarbons

Also suitable are hydrocarbons such as petrolatum, microcrystalline wax, hydrogenated polyisobutene, paraffin, red petrolatum, squalene, squalane, and the like.

(6) Oleaginous Materials

Also suitable as the oil phase gelling agent are one or more oleaginous compounds which are solid or semi-solid at room temperature and have a melting point of 32 to 100° C. Examples of such materials include lanolin and derivatives thereof such as lanolin alcohol, acetylated lanolin alcohol; or hydrogenated oils, such as hydrogenated castor oil, or alkoxylated hydrogenated castor oil. Preferably, one of the oil phase gelling agents is PEG-40 hydrogenated castor oil.

(7) Animal and Plant Waxes

Also suitable as the oil phase gelling agent are one or more animal or plant waxes. Examples of such compounds include apple wax, avocado wax, bayberry wax, carnauba wax, ceresin, beeswax, hydrogenated jojoba oil, hydrogenated jojoba wax, hydrogenated rice bran wax, hydrolyzed beeswax, jojoba butter, jojoba esters, jojoba wax, lanolin wax, mink wax, montan acid wax, montan wax, ouricury wax, ozokerite, palm kemal wax, PEG-5–20 beeswax, PEG-12 carnauba, Rice wax, shellac wax, spent grain wax, sulfurized jojoba oil, synthetic beeswax, synthetic candellila wax, synthetic carnauba, synthetic jojoba wax, and mixtures thereof.

(8) Hydrophobically Modified Materials

Also suitable are hydrophobically modified materials such as hydrophobically modified silica, i.e. silica modified by substitution of a sufficient number of the hydroxyl groups with hydrophobic $C_{1-4}$ alkyl groups, preferably methyl. Also, the polysaccharides which are mentioned as suitable for use in gelling the aqueous phase of the composition may be suitable for gelling the oil phase if they are hydrophobically modified so that they become oil soluble rather than water soluble. The term "hydrophobically modified" means that the polysaccharides are reacted with certain other compounds that confer hydrophobicity to the polysaccharide. An example of such a reaction would be the esterification of the hydroxyl groups on the polysaccharide with fatty acids.

Preferably, in the cosmetic stick compositions of the invention the oil phase gelling agent is synthetic wax or PEG-40 hydrogenated castor oil, or mixtures thereof.

III. Emollient Oil

The compositions of the invention comprise 0.1–30%, preferably 0.5–25%, more preferably 1–20% by weight of the total composition of one or more emollient oils which are liquids at room temperature. The oil may be volatile or non-volatile. The term "volatile" means that the oil has a measureable vapor pressure, or a vapor pressure of at least 2 mm. of mercury at 20° C. The term "nonvolatile" means that the oil has a vapor pressure of less than 2 mm. of mercury at 20° C. If the cosmetic compositions of the invention are transfer resistant sticks, it is desireable to use significant amounts of volatile solvent for the oil component. Suitable volatile solvents or oils are liquids, and enable easy formulation of the cosmetic stick of the invention. When the cosmetic stick product of the invention is applied to skin or lips, the volatile solvent of the invention must be capable of flashing off to leave the other ingredients in the stick on the skin. Suitable volatile solvents generally have a viscosity of 0.5 to 10 centistokes at 25° C. Suitable volatile oils include linear silicones, cyclic silicones, paraffinic hydrocarbons, or mixtures thereof.

Cyclic silicones (or cyclomethicones) are of the general formula:

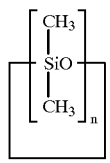

where n=3–7. Linear volatile silicones in accordance with the invention have the general formula:

where n=0–7, preferably 0–5.

Linear and cyclic volatile silicones are available from various commercial sources including Dow Coming Corporation and General Electric. The Dow Coming volatile silicones are sold under the tradenames Dow Coming 244, 245, 344, and 200 fluids. These fluids comprise octamethylcyclotetrasiloxane, decamethylcyclopentasiloxane, hexamethyldisiloxane, and mixtures thereof.

Also suitable as the volatile oils are various straight or branched chain paraffinic hydrocarbons having 5 to 40 carbon atoms, more preferably 8–20 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70–225, preferably 160 to 190 and a boiling point range of 30 to 320, preferably 60–260 degrees C., and a viscosity of less than 10 cs. at 25 degrees C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Another $C_{12}$ isoparaffin (isododecane) isidistributed by Presperse under the tradename Permethyl 99A. Various $C_{16}$ isoparaffins commercially available, such as isohexadecane (having the tradenamne Permethyl R), are also suitable. Transfer resistant cosmetic sticks of the invention will generally comprise a mixture of volatile silicones and volatile paraffinic hydrocarbons.

A wide variety of nonvolatile oils are also suitable for use in the cosmetic compositions of the invention. The nonvolatile oils generally have a viscosity of greater than 10 centipoise at 25° C., and may range in viscosity up to 1,000,000 centipoise at 25° C. Examples of nonvolatile oils suitable for use in the cosmetic sticks of the invention include esters of the formula RCO—OR' wherein R and R' are each independently a $C_{1-25}$, preferably a $C_{4-20}$ straight or branched chain alkyl, alkenyl or alkoxycarbonylalkyl or alkylcarbonyloxyalkyl. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, as well as the esters disclosed on pages 24–26 of the *C.T.F.A. Cosmetic Ingredient Handbook*, First Edition, 1988, which is hereby incorporated by reference.

The oil may also comprise naturally occuring glyceryl esters of fatty acids, or triglycerides. Both vegetable and animal sources may be used. Examples of such oils include castor oil, lanolin oil, triisocetyl citrate, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

Also suitable as the oil are synthetic or semi-synthetic glyceryl esters, e.g. fatty acid mono-, di-, and triglycerides which are natural fats or oils that have been modified, for example, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

Also suitable as the oil are nonvolatile hydrocarbons such as isoparaffins, mineral oil, and so on.

Nonvolatile silicones, both water soluble and water insoluble, are also suitable as the oil component. Such silicones preferably have a viscosity of 10 to 600,000 centistokes, preferably 20 to 100,000 centistokes at 25° C. Suitable water insoluble silicones include amodimethicone, bisphenylhexarnethicone, dimethicone, hexadecyl methicone, methicone, phenyl trimethicone, simethicone, dimethylhydrogensiloxane, vinyldimethicone, and mixtures thereof. Also suitable are water soluble silicones such as dimethicone copolyol, dimethiconol, and the like. Such silicones are available from Dow Corning as the 3225C formulation aid, Dow 190 and 193 fluids, or similar products marketed by Goldschmidt under the ABIL tradename.

Also suitable as the nonvolatile oil are various fluorinated oils such as fluorinated silicones, fluorinated esters, or perfluropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. Perfluoropolyethers like those disclosed in U.S. Pat. Nos. 5,183,589, 4,803,067, 5,183,588 all of which are hereby incorporated by reference, which are commercially available from Montefluos under the trademark Fomblin, are also suitable shine enhancers.

Guerbet esters are also suitable oils. The term "guerbet ester" means an ester which is formed by the reaction of a guerbet alcohol having the general formula:

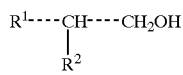

with a carboxylic acid having the general formula:

$R^3COOH$, or $HOOC-R^3-COOH$ wherein $R^1$ and $R^2$ are each independently a $C_{4-20}$ alkyl and $R^3$ is a substituted or unsubstituted fatty radical such as a $C_{1-50}$ straight or branched chain saturated or unsaturated alkyl or alkylene, or phenyl, wherein the substituents are halogen, hydroxyl, carboxyl, and alkylcarbonylhydroxy. Particularly preferred is a carboxylic acid wherein the R group is such to provide an ingredient known as meadowfoam seed oil.

Preferably, the guerbet ester is a fluoro-guerbet ester which is formed by the reaction of a guerbet alcohol and carboxylic acid (as defined above), and a fluoroalcohol having the following general formula:

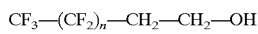

wherein n is from 3 to 40.
Examples of suitable fluoro guerbet esters are set forth in U.S. Pat. No. 5,488,121 which is hereby incorporated by reference. Suitable fluoro-guerbet esters are also set forth in U.S. Pat. No. 5,312,968 which is hereby incorporated by reference. Most preferred is a guerbet ester having the tentative CTFA name fluoro-octyldodecyl meadowfoarnate. This ester is sold by Siltech, Norcross Ga. as Developmental Ester L61125A, under the tradename Silube GME-F.

Preferably, the compositions of the invention contain one or more nonvolatile oils, preferably water insoluble nonvolatile silicones such as dimethicone.

IV. Surfactants

Surfactants are particularly desireable to wet the pigments and assist in stabilizing the emulsion compositions. Generally, if surfactants are present, a range of 0.001–20%, preferably 0.01–10%, more preferably 0.05–8% by weight of the total composition is suggested. Suitable surfactants may be organic, or silicone-based, and include nonionic, amphoteric, zwitterionic, and cationic surfactants.

A. Silicone Surfactants

Silicone surfactants, or emulsifiers, may be used in the compositions of the invention. They may be liquid or solid at room temperature. The surfactant is generally a water-in-oil or oil-in-water type surfactant which is preferably nonionic, having an Hydrophile/Lipophile Balance (HLB) of 2 to 18. Preferably the silicone surfactant is nonionic and has an HLB of 2 to 12, preferably 2 to 10, most preferably 4 to 6. The HLB of a nonionic surfactant is the balance between the hydrophilic and lipophilic portions of the surfactant and is calculated according to the following formula:

$$HLB = 7 + 11.7 \times \log M_w/M_o$$

where $M_w$ is the molecular weight of the hydrophilic group portion and $M_o$ is the molecular weight of the lipophilic group portion.

The surfactant is an organosiloxane polymer. The term "organosiloxane polymer" means a polymer containing a polymeric backbone including repeating siloxy units that may have cylic, linear or branched repeating units, e.g. di(lower)alkylsiloxy units, preferably dimethylsiloxy units. The hydrophilic portion of the organosiloxane is generally achieved by substitution onto the polymeric backbone of a radical that confers hydrophilic properties to a portion of the molecule. The hydrophilic radical may be substituted on a terminus of the polymeric organosiloxane, or on any one or more repeating units of the polymer. In general, the repeating dimethylsiloxy units of modified polydimethylsiloxane emulsifiers are lipophilic in nature due to the methyl groups, and confer lipophilicity to the molecule. In addition, longer chain alkyl radicals, hydroxy-polypropyleneoxy radicals, or other types of lipophilic radicals may be substituted onto the siloxy backbone to confer further lipophilicity and organo-compatibility. If the lipophilic portion of the molecule is due in whole or part to a specific radical, this lipophilic radical may be substituted on a terminus of the organosilicone polymer, or on any one or more repeating units of the polymer. It should also be understood that the organosiloxane polymer in accordance with the invention should have at least one hydrophilic portion and one lipophilic portion.

The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, sulfonates, sulfates, phosphates, or amines.

The term "lipophilic radical" means an organic radical that, when substituted onto the organosiloxane polymer backbone, confers lipophilic properties to the substituted portion of the polymer. Examples of organic radicals which will conver lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof. The $C_{1-40}$ alkyl may be non-interrupted, or interruped by one or more oxygen atoms, a benzene ring, amides, esters, or other functional groups.

The polymeric organosiloxane emulsifier used in the invention may have any of the following general formulas:

$M_xQ_y$, or $M_xT_y$, or $MD_xD'_yD''_zM$ wherein each M is independently a substituted or unsubstituted trimethylsiloxy endcap unit. If substituted, one or more of the hydrogens on the endcap methyl groups are substituted, or one or more methyl groups are substituted with a substituent that is a lipophilic radical, a hydrophilic radical, or mixtures thereof. T is a trifunctional siloxy unit having the empirical formula RR'SiO$_{1.5}$ or RRSiO$_{1.5}$. Q is a quadrifunctional siloxy unit having the empirical formula SiO$_2$, and D, D', D", x, y, and z are as set forth below, with the proviso that the compound contains at least one hydrophilic radical and at least one lipophilic radical. Examples of emulsifiers used in the compositions of the invention are of the general formula:

$$MD_xD'_yD''_zM$$

wherein the trimethylsiloxy endcap unit is unsubstituted or mono-substituted, wherein one methyl group is substituted with a lipophilic radical or a hydrophilic radical. Examples of such substituted trimethylsiloxy endcap units include $(CH_3)_2HPSiO$, $(CH_3)_2LPSiO$, $(CH_3)_2CH_2HPSiO$, $(CH_3)_2CH_2LPSiO$, wherein HP is a hydrophilic radical and LP is a lipophilic radical. D, D', and D" are difunctional siloxy units substituted with methyl, hydrogen, a lipophilic radical, a hydrophilic radical or mixtures thereof. In this general formula:

x=0–5000, preferably 1–1000
y=0–5000, preferably 1–1000, and
z=0–5000, preferably 0–1000, with the proviso that the compound contains at least one lipophilic radical and at least one hydrophilic radical. Examples of these polymers are disclosed in U.S. Pat. No. 4,698,178, which is hereby incorporated by reference.

Particularly useful are linear silicones having the general formula:

$$MD_xD'_yD''_zM$$

wherein M=RRRSiO$_{1/2}$
D and D'=RR'SiO$_{2/2}$
D"=RRSiO$_{2/2}$
x, y, and z are each independently 0–1000,
where R is methyl or hydrogen, and R' is a hydrophilic radical or a lipophilic radical, with the proviso that the compound contains at least one hydrophilic radical and at least one lipophilic radical.

Most preferred is wherein
M=trimethylsiloxy
D Si[(CH$_3$)][(CH$_2$)$_n$CH$_3$]O$_{2/2}$ where n=1–40,
D'=Si [(CH$_3$)][(CH$_2$)$_o$—O—PE)]O$_{2/2}$ where PE is (—C$_2$H$_4$O)$_a$(—C$_3$H$_6$O)$_b$H, o=0–40,
a=1–100 and b=1–100, and
D"=Si (CH$_3$)$_2$O$_{2/2}$ Typical examples of preferred organosiloxane emulsifiers in accordance with the invention include those set forth below:

I.

$$CH_3-\underset{\underset{CH_3}{|}}{\overset{\overset{CH_3}{|}}{Si}}-O-\left[\underset{\underset{LP}{|}}{\overset{\overset{CH_3}{|}}{Si}}-O\right]_x\left[\underset{\underset{HP}{|}}{\overset{\overset{CH_3}{|}}{Si}}-O\right]_y\left[\underset{\underset{CH_3}{|}}{\overset{\overset{CH_3}{|}}{Si}}-O\right]_z\underset{\underset{CH_3}{|}}{\overset{\overset{CH_3}{|}}{Si}}-CH_3$$

II.

$$CH_3-\underset{\underset{LP}{|}}{\overset{\overset{CH_3}{|}}{Si}}-O-\left[\underset{\underset{HP}{|}}{\overset{\overset{CH_3}{|}}{Si}}-O\right]_y\left[\underset{\underset{CH_3}{|}}{\overset{\overset{CH_3}{|}}{Si}}-O\right]_z\underset{\underset{CH_3}{|}}{\overset{\overset{CH_3}{|}}{Si}}-CH_3$$

III.

$$CH_3-\underset{\underset{HP}{|}}{\overset{\overset{CH_3}{|}}{Si}}-O-\left[\underset{\underset{LP}{|}}{\overset{\overset{CH_3}{|}}{Si}}-O\right]_x\left[\underset{\underset{CH_3}{|}}{\overset{\overset{CH_3}{|}}{Si}}-O\right]_z\underset{\underset{CH_3}{|}}{\overset{\overset{CH_3}{|}}{Si}}-CH_3$$

IV.

$$CH_3-\underset{\underset{HP}{|}}{\overset{\overset{CH_3}{|}}{Si}}-O-\left[\underset{\underset{CH_3}{|}}{\overset{\overset{CH_3}{|}}{Si}}-O\right]_z\underset{\underset{LP}{|}}{\overset{\overset{CH_3}{|}}{Si}}-CH_3$$

V.

(cage-like silsesquioxane structure with HP, Si(CH$_3$)$_3$, Si(CH$_3$)$_2$LP, and Si(CH$_3$)$_3$ substituents)

wherein LP is a lipophilic radical
HP is a hydrophilic radical
x is 0–5000
y is 0–5000, and
z is 0–5000, with the proviso that the organosiloxane contains at least on hydrophilic radical and at least one lipophilic radical.

More preferred are compounds of the generic formula I wherein LP is a lipophilic radical which is a C$_{1-40}$ straight or branched chain alkyl, HP is a hydrophilic radical containing hydroxy-polyethyleneoxy, and z is at least 1. Most preferred is a compound of the formula:

$$CH_3-\underset{\underset{CH_3}{|}}{\overset{\overset{CH_3}{|}}{Si}}-O-\left[\underset{\underset{(CH_2)_p}{|}\atop\underset{CH_3}{|}}{\overset{\overset{CH_3}{|}}{Si}}-O\right]_x\left[\underset{\underset{(CH_2)_3}{|}\atop\underset{O}{|}\atop\underset{PE}{|}}{\overset{\overset{CH_3}{|}}{Si}}-O\right]_y\left[\underset{\underset{CH_3}{|}}{\overset{\overset{CH_3}{|}}{Si}}-O\right]_z\underset{\underset{CH_3}{|}}{\overset{\overset{CH_3}{|}}{Si}}-CH_3$$

wherein p is 10–40, preferably 12–20, most preferably 15, and PE is (—C$_2$H$_4$O)$_a$(—C$_3$H$_6$O)$_b$—H
where x, y, z, a, and b are such that the maximum molecular weight of the polymer is approximately 50,000. Organosiloxane polymers useful in the compositions of the invention are commercially available from Goldschmidt Corporation under the ABIL tradename. The preferred polymer is cetyl dimethicone copolyol and has the tradename ABIL WE 09 or ABIL WS 08. The cetyl dimethicone copolyol may be used alone or in conjunction with other non-silicone organic emulsifiers, for example, blends of 25–50% of the organosiloxane emulsifier, 25–50% of a non-silicone organic emulsifier, and 25–50% by weight emollients or oils are suitable. Materials are identified by the C.T.F.A. names cetyl dimethicone copolyol (and) polyglyceryl 4-isostearate (and) hexyl laurate, or cetyl dimethicone copolyol (and) polyglyceryl-3 oleate (and) hexyl laurate both work well.

These blends contain approximately 25–50% of each ingredient, for example ABIL WE 09 contains approximately, by weight of the total ABIL composition, 25–50% cetyl dimethicone copolyol, 25–50%, polyglyceryl 4-isostearate, and 25–50% of hexyl laurate which is an emollient or oil.

Another type of preferred organosiloxane emulsifier suitable for use in the compositions of the invention are emulsifiers sold by Union Carbide under the Silwet™ trademark. These emulsifiers are represented by the following generic formulas:

wherein PE=—$(EO)_m(PO)_nR$
R=lower alkyl or hydrogen
Me=methyl
EO is polyethyleneoxy
PO is polypropyleneoxy
m and n are each independently 1–5000
x and y are each independently 0–5000, and

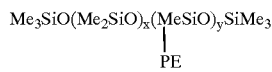

wherein PE=—$CH_2CH_2CH_2O(EO)_m(PO)_nZ$
Z=lower alkyl or hydrogen, and
Me, m, n, x, y, EO and PO are as described above, with the proviso that the molecule contains a lipophilic portion and a hydrophilic portion. Again, the lipophilic portion can be supplied by a sufficient number of methyl groups on the polymer backbone.

Particularly preferred is a Silwet™ polymer of the following general formula:

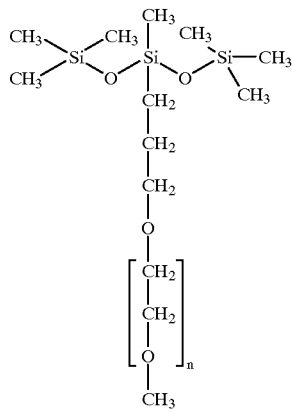

Wherein n is 1–10, preferably 8.

Another preferred organosiloxane emulsifier for use in the compositions of the invention is dimethicone copolyol.

Examples of other polymeric organosiloxane surfactants or emulsifiers include amino/polyoxyalkyleneated polydiorganosiloxanes disclosed in U.S. Pat. No. 5,147,578. Also suitable are organosiloxanes sold by Goldschmidt under the ABIL trademark including ABIL B-9806, as well as those sold by Rhone-Poulenc under the Alkasil tradename. Also, organosiloxane emulsifiers sold by Amerchol under the Amersil tradename, including Amersil ME-358, Amersil DMC-287 and Amersil DMC-357 are suitable. Dow Corning surfactants such as Dow Corning 3225C Formulation Aid, Dow Corning 190 Surfactant, Dow Corning 193 Surfactant, Dow Corning Q2-5200, and the like are also suitable. In addition, surfactants sold under the tradename Silwet by Union Carbide, and surfactants sold by Troy Corporation under the Troysol tradename, those sold by Taiwan Surfactant Co. under the tradename Ablusoft, those sold by Hoechst under the tradename Arkophob, are also suitable for use in the invention.

B. Organic Surfactants

Organic surfactants are also suitable for use in the invention, in particular nonionic, amphoteric, zwitterionic, or anionic surfactants. Particularly preferred are nonionic organic surfactants having an HLB of 2 to 16, preferably 4–12.

(1) Nonionic Organic Surfactants

A wide variety of nonionic organic surfactants are suitable. Nonionic surfactants are generally compounds produced by the condensation of alkylene oxide groups with a hydrophobic compound. Classes of nonionic surfactants are:

(a) Long chain dialkyl sulfoxides containing one short chain alkyl or hydroxy alkyl radical of from about 1 to 3 carbon atoms and one long hydrophobic chain which may be an alkyl, alkenyl, hydroxyalkyl, or ketoalkyl radical containing from about 8 to 20 carbon atoms, from 0 to 10 ethylene oxide moieties, and 0 or 1 glyceryl moiety.

(b) Polysorbates, such as sucrose esters of fatty acids. Examples of such materials include sucrose cocoate, sucrose behenate, and so on.

(c) Polyethylene oxide condensates of alkyl phenols, for example the condensation products of alkyl phenols having an alkyl group of 6 to 20 carbon atoms with ethylene oxide being present in amounts of about 10 to 60 moles of ethylene oxide per mole of alkyl phenol.

(d) Condensation products of ethylene oxide with the reaction product of propylene oxide and ethylene diamine.

(e) Condensation products of aliphatic alcohols having 8 to 18 carbon atoms with ethylene oxide, for example a coconut alcohol/ethylene oxide condensate having 10 to 30 moles of ethylene oxide per mole of coconut alcohol, the coconut alcohol fraction having 10 to 14 carbon atoms.

(f) Long chain tertiary amine oxides such as those corresponding to the general formula:

$R_1R_2R_3NO$ wherein $R_1$ contains an alkyl, alkenyl or monohydroxyalkyl radical ranging from about 8 to 18 carbon atoms in length, from 0 to about 10 ethylene oxide moieties, and from 0 to about 1 glyceryl moiety and $R_2$ and $R_3$ are each alkyl or monohydroxyalkyl groups containing from about 1 to about 3 carbon atoms.

(g) Long chain tertiary phosphine oxides corresponding to the general formula:

$RR_1R_2PO$ wherein R contains an alkyl, alkenyl, or monohydroxyalkyl radical having 8 to 18 carbon atoms, from 0–10 ethylene oxide moieties and 0 or 1 glyceryl moiety, and $R_2$ and $R_3$ are each alkyl or monohydroxyalkyl group containing from about 1 to 3 carbon atoms.

(h) Alkyl polysaccharides having a hydrophobic group of 6 to 30, preferably 10, carbon atoms and a polysaccharide group such as glucose, galactose, etc. Suitable alkyl polysaccharides are octyl, nonydecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses, and so on.

(i) Polyethylene glycol (PEG) glyceryl fatty esters, having the formula $$RC(O)OCH_2CH(OH)CH_2(OCH_2CH_2)_nOH$$

wherein n is 5–200 and RC(O)— is a hydrocarbylcarbonyl group wherein R is preferably an aliphatic radical having 7 to 19 carbon atoms. Particularly preferred are polyethylene glycol ethers of sugar mono- and diesters, i.e. which are obtained by reaction of sugars with fatty acids. Examples are PEG-20 methyl glucose sesquiisostearate, PEG-20 methyl glycose sesquilaurate, and mixtures thereof.

(j) Other nonionic surfactants that may be used include $C_{10-18}$ alkyl($C_{1-6}$)polyhydroxy fatty acid amides such as $C_{12-18}$ methylglucamides, N-alkoxy polyhydroxy fatty acid amides, N-propyl through N-hexyl $C_{12-18}$ glucamides and so on.

Particularly preferred for use in the compositions of the invention are alkoxylated fatty esters of sugar or derviatives of sugar, in particular PEG-20 methyl glucose sesquiisostearate.

(2) Amphoteric Organic Surfactants

Amphoteric surfactants that can be used in the compositions of the invention are generally described as derivatives of aliphatic secondary or tertiary amines wherein one aliphatic radical is a straight or branched chain alkyl of 8 to 18 carbon atoms and the other aliphatic radical contains an anionic group such as carboxy, sulfonate, sulfate, phosphate, or phosphonate.

Suitable amphoteric surfactants may be imidazolinium compounds having the general formula:

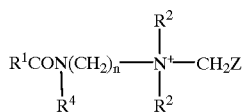

wherein $R^1$ is $C_{8-22}$ alkyl or alkenyl, preferably $C_{12-16}$; $R^2$ is hydrogen or $CH_2CO_2M$, $R^3$ is $CH_2CH_2OH$ or $CH_2CH_2OCH_2CHCOOM$; $R^4$ is hydrogen, $CH_2CH_2OH$, or $CH_2CH_2OCH_2CH_2COOM$, Z is $CO_2M$ or $CH_2CO_2M$, n is 2 or 3, preferably 2, M is hydrogen or a cation such as an alkali metal, alkaline earth metal, ammonium, or alkanol ammonium. cation. Examples of such materials are marketed under the tradename MIRANOL, by Miranol, Inc.

Also suitable amphoteric surfactants are monocarboxylates or dicarboxylates such as cocamphocarboxypropionate, cocoamphocarboxypropionic acid, cocamphocarboxyglycinate, and cocoamphoacetate.

Other types of amphoteric surfactants include aminoalkanoates of the formula $$R-NH(CH_2)_nCOOM$$

or iminodialkanoates of the formula:

$$R-N[(CH_2)_mCOOM]_2$$

and mixtures thereof; wherein n and m are 1 to 4, R is $C_{8-22}$ alkyl or alkenyl, and M is hydrogen, alkali metal, alkaline earth metal, ammonium or alkanolammonium. Examples of such amphoteric surfactants include n-alkylaminopropionates and n-alkyliminodipropionates, which are sold under the trade name MIRATAINE by Miranol, Inc. or DERIPHAT by Henkel, for example N-lauryl-beta-amino propionic acid, N-lauryl-beta-iminodipropionic acid, or mixtures thereof.

(3) Zwitterionic Organic Surfactants

Zwitterionic surfactants are also suitable for use in the compositions of the invention.

The general formula for such surfactants is:

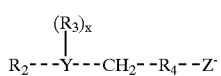

wherein $R_2$ contains an alkyl, alkenyl or hydroxy alkyl radical of from about 8 to about 18 carbon atoms, from 0 to about 10 ethylene oxide moieties and 0 or 1 glyceryl moiety; Y is selected from the group consisting of nitrogen, phosphorus, and sulfur atoms; $R_3$ is an alkyl or monohydroxyalkyl group containing about 1 to 3 carbon atoms; X is 1 when Y is a sulfur atom, and 2 when Y is a nitrogen or phosphorus atom; $R_4$ is an alkylene or hydroxyalkylene of from about 1 to about 4 carbon atoms, and Z is a radical selected from the group consisting of carboxylate, sulfonate, sulfate, phosphonate, and phosphate groups.

Zwitterionics include betaines, for example higher alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxylethyl betaine, and mixtures thereof. Also suitable are sulfo- and amido- betaines such as coco dimethyl sulfopropyl betaine, stearyl dimethyl sulfopropyl betaine, and the like.

(4) Anionic Surfactants

Anionic surfactants include alkyl and alkyl ether sulfates generally having the formula $ROSO_3M$ and $RO(C_2H_4O)SO_3M$ wherein R is alkyl or alkenyl of from about 10 to 20 carbon atoms, x is 1 to about 10 and M is a water soluble cation such as ammonium, sodium, potassium, or triethanolamine cation.

Another type of anionic surfactant which may be used in the compositions of the invention are water soluble salts of organic, sulfuric acid reaction products of the general formula:

$$R_1-SO_3-M$$

wherein $R_1$ is chosen from the group consisting of a straight or branched chain, saturated aliphatic hydrocarbon radical having from about 8 to about 24 carbon atoms, preferably 12 to about 18 carbon atoms; and M is a cation. Examples of such anionic surfactants are salts of organic sulfuric acid reaction products of hydrocarbons such as n-paraffins having 8 to 24 carbon atoms, and a sulfonating agent, such as sulfur trioxide.

Also suitable as anionic surfactants are reaction products of fatty acids esterified with isethionic acid and neutralized with sodium hydroxide. The fatty acids may be derived from coconut oil, for example.

In addition, succinates and succinimates are suitable anionic surfactants. This class includes compounds such as disodium N-octadecylsulfosuccinate; tetrasodium N-(1,2-dicarboxyethyl)-N-octadecylsulfosuccinate; and esters of sodium sulfosuccinic acid e.g. the dihexyl ester of sodium sulfosuccinic acid, the dioctyl ester of sodium sulfosuccinic acid, and the like.

Other suitable anionic surfactants include olefin sulfonates having about 12 to 24 carbon atoms. The term "olefin sulfonate" means a compound that can be produced by sulfonation of an alpha olefin by means of uncomplexed sulfur trioxide, followed by neutralization of the acid reaction mixture in conditions such that any sultones which have been formed in the reaction are hydrolyzed to give the corresponding hydroxy-alkanesulfonates. The alpha-olefin from which the olefin sulfonate is derived is a mono-olefin having about 12 to 24 carbon atoms, preferably about 14 to 16 carbon atoms.

Other classes of suitable anionic organic surfactants are the beta-alkoxy alkane sulfonates or water soluble soaps thereof such as the salts of $C_{10-20}$ fatty acids, for example coconut and tallow based soaps. Preferred salts are ammonium, potassium, and sodium salts.

Still another class of anionic surfactants include N-acyl amino acid surfactants and salts thereof (alkali, alkaline earth, and ammonium salts) having the formula:

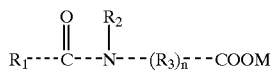

wherein $R_1$ is a $C_{8-24}$ alkyl or alkenyl radical, preferably $C_{10-18}$; $R_2$ is H, $C_{1-4}$ alkyl, phenyl, or —$CH_2COOM$; $R_3$ is $CX_2$- or $C_{1-2}$ alkoxy, wherein each X independently is H or a $C_{1-6}$ alkyl or alkylester, n is from 1 to 4, and M is H or a salt forming cation as described above. Examples of such surfactants are the N-acyl sarcosinates, including lauroyl sarcosinate, myristoyl sarcosinate, cocoyl sarcosinate, and oleoyl sarcosinate, preferably in sodium or potassium forms.

(5) Cationic Surfactants

It is also possible to include cationic surfactants in the composition of the invention provided they are compatible with the other ingredients in the composition. Cationic quaternary amines or ammonium compounds may be used, as well as cationic silicones such as amodimethicone.

V. Particulate Matter

The composition of the invention may contain 0.1–50%, preferably 0.5–40%, more preferably 1–25% by weight of the total composition, of particulate matter having a particle size of 0.02 to 100, preferably 0.5 to 100, microns. The particulate matter may be colored or non-colored (for example white). Suitable particulates include bismuth oxychloride, titanated mica, a fumed silica, spherical silica, polymethylmethacrylate, polyethylene, polypropylene, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone oil or various other agents either alone or in combination, which coat the powder surface and render the particles more lipophilic in nature.

The particulates may also include various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes, in particular the Lakes of D&C and FD&C colors. Inorganic pigments include iron oxides, ultramarines, chromium, chromium hydroxide colors, and mixtures thereof.

Preferably the composition will contain both pigmented and non-pigmented particulates. Obviously the percentage of pigments used in the particulate phase will depend on the type of cosmetic being formulated. Color cosmetics generally have a much higher concentration of color than other types of cosmetics. Generally the weight ratio of pigmented to non-pigmented particulates range from 1:50 to 50:1. It should be noted that particulates that are white or have no color are considered non-pigmented particulates in accordance with the invention, while particulates which exhibit color other than white are considered pigmented particulates in accordance with the invention.

It may be desired that the particulates be surface coated or surface treated with materials which provide hydrophobicity to the particle surface. Examples of such coatings include silicones, lecithin, perfluoropolymethyl isopropyl ether, fluorinated silicones, lecithin, and the like. Particularly preferred are silicone treated pigments as disclosed in U.S. Pat. No. 5,143,722, as well as pigments which are coated with perfluoropolymethyl isopropyl ether.

The compositions contain 5–95%, preferably 10–90%, more preferably 15–80% water. While the cosmetic sticks of the invention may be found in the water-in-oil or oil-in-water emulsion form, preferably they are in the form of oil-in-water emulsions. Accordingly, they provide a very light fresh feel when applied to skin or lips.

VI. Other Ingredients

A variety of other ingredients may be added to the compositions to improve their aesthetic and treatment properties. For example, vitamins, humectants, preservatives, antioxidants, and so on, are desireable.

(A) Sunscreens

The compositions of the invention may contain 0.001–20%, preferably 0.01–10%, more preferably 0.05–8% of one or more sunscreens. A sunscreen is defined as an ingredient that absorbs at least 85 percent of the light in the UV range at wavelengths from 290 to 320 nanometers, but transmit UV light at wavelengths longer than 320 nanometers. Sunscreens generally work in one of two ways. Particulate materials, such as zinc oxide or titanium dioxide, as mentioned above, physically block ultraviolet radiation. Chemical sunscreens, on the other hand, operate by chemically reacting upon exposure to UV radiation. Suitable sunscreens that may be included in the compositions of the invention are set forth on page 582 of the *CTFA Cosmetic Ingredient Handbook*, Second Edition, 1992, as well as U.S. Pat. No. 5,620,965, both of which are hereby incorporated by reference. Examples of such sunscreen materials are p-aminobenzoic acid (PABA), cinoxate, diethanolamine p-methoxycinnamate (DEA-methoxycinnamate), Digalloyl trioleate, dioxybenzone (Benzophenone-8), ethyl 4-[bis-(hydroxypropyl)] amnobenzoate (ethyl dihydroxypropyl PABA), 2-ethylhexyl-2-cyano- 3,3-diphenylacrylate (octocrylene), ethylhexyl p-methoxycinnamate (Octyl methoxycinnamate), 2-ethylhexyl salicylate (Octyl salicylate), glyceryl aminobenzoate (Glyceryl PABA), homosalate, lawsone with dihydroxyacetone, menthyl anthranilate, oxybenzone (Benzophenone-3), Padimate A (Pentyl Dimethyl PABA), Padimate 0, (Octyl Dimethyl PABA), 2-Phenylbenzimidazole-5-sulfonic acid (Phenylbenzimidazole Sulfonic acid), Red Petrolatum, Sulisobenzone (Benzophenone-4), triethanolamine salicylate (TEA-Salicylates), and so on.

(B). Preservatives

The composition may contain 0.0001–8%, preferably 0.001–6%, more preferably 0.005–5% by weight of the total composition of preservatives. A variety of preservatives are suitable, including such as benzoic acid, benzyl alcohol, benzylhemiformal, benzylparaben, 5-bromo-5-nitro-1,3-dioxane, 2-bromo-2-nitropropane-1,3-diol, butyl paraben, calcium benzoate, calcium propionate, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, and all of those disclosed on pages 570 to 571 of the CTFA Cosmetic Ingredient Handbook, Second Edition, 1992, which is hereby incorporated by reference.

(C). Vitamins and Antioxidants

The compositions of the invention may contain vitamins and/or coenzymes, as well as antioxidants. If so, 0.001–10%, preferably 0.01–8%, more preferably 0.05–5% by weight of the total composition are suggested. Suitable vitamins include the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are Vitamin A palmitate, acetate, or other esters thereof, as well as Vitamin A in the form of beta carotene. Also suitable is Vitamin E and derivatives thereof such as Vitamin E acetate, nicotinate, or other esters thereof. In addition, Vitamins D and K are suitable.

Suitable antioxidants are ingredients which assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and so on.

(D). Alpha or beta hydroxy acids, alpha keto acids

It may be desired to add one or more alpha or beta hydroxy acids or alpha ketoacids to the compositions of the invention. Suggested ranges are 0.01–20%, preferably 0.1–15%, more preferably 0.5–10% by weight of the total composition. Suitable alpha hydroxy acids and alpha ketoacids are disclosed in U.S. Pat. No. 5,091,171, which is hereby incorporated by reference. Such alpha hydroxy acids are as follows:

a) Organic carboxylic acids where one hydroxyl group is attached to the alpha carbon atom of the acid. The general structure of such alpha hydroxy acids may be represented by the following formula:

(Ra)(Rb)C(OH)COOH wherein Ra and Rb are H, F, Cl, Br, alkyl, aralkyl, or aryl group of saturated, unsaturated, straight or branched chain or cyclic form having 1–10 carbon atoms, and in addition Ra or Rb may carry OH, CHO, COOH and alkoxy groups having 1 to 9 carbon atoms.

The second group of alpha hydroxy acids may be represented by the following formula:

(Ra)CO COO(Rb)

wherein Ra and Rb are H, alkyl, aralkyl, or aryl groups of straight or branched chain saturated or unsaturated alkyl having 1 to 10 carbon atoms, and in addition Ra may carry F, Cl, Br, I, OH, CHO, COOH, and alkoxy groups having 1 to 10 carbon atoms.

The alpha hydroxy acids may exist in the keto acid form, or the ester form. Examples of such alpha hydroxy acids include glycolic acid, malic acid, pyruvic acid, mandelic acid, lactic acid, methyllactic acid, and so on.

Also beta hydroxy acids such as salicylic acid, and derivatives thereof may be included in the compositions of the invention.

The invention will be further described in connection with the following examples which are set forth for the purpose of illustration only.

EXAMPLE 1

An oil-in-water emulsion stick make-up was made according to the following formula:

|   |   | w/w % |
|---|---|---|
| 1 | Dimethicone | 12.44 |
| 2 | Titanium dioxide | 4.80 |
| 2 | Polyglyceryl-6-polyricinoleate | 0.39 |
| 2 | Aluminum stearate | 0.62 |
| 2 | Cyclomethicone | 3.51 |
| 3 | Propyl paraben | 0.10 |
| 4 | Iron oxide yellow* | 1.00 |
| 4 | Iron oxide red* | 0.20 |
| 4 | Iron oxide black* | 0.08 |
| 4 | Talc | 0.85 |
| 4 | Nylon-12 | 0.25 |
| 5 | Synthetic wax | 1.50 |
| 5 | Isostearyl alcohol | 5.70 |
| 5 | Hydrogenated castor oil | 1.50 |
| 6 | Water | 41.03 |
| 7 | Ascorbic acid | 0.10 |
| 8 | Sodium stearate | 7.55 |
| 9 | Butylene glycol | 13.00 |
| 10 | Methyl paraben | 0.30 |
| 11 | PEG-20 methyl glycosesquiisostearate | 3.49 |
| 12 | PPC** | 0.86 |
| 13 | 10% calcium chloride solution | 0.23 |
| 14 | Phenoxyethanol | 0.50 |
| 15 | Tocopheryl acetate | 0.10 |
| 16 | Retinyl palmitate | 0.10 |
| 17 | Ethylene brassylate | 0.15 |

*pigments coated with perfluoropolymethyl isopropyl ether.
**the PPC was a complex of casein and carageenan in a weight ratio of about 20 percent casein and 80 percent carageenan by weight of the total PPC The pigment grind was made by mixing, in an open colloid mill Sequences 1, 2, 3, and 4 and the dispersion was checked between two glass slides. The Sequence 5 ingredients were then added and the mixture heated to 85 to 87° C. using a propellar mixer until the mixture was smooth and uniform. In a separate container, Sequence 6 was heated to 90° C. Sequences 7 through 12 were added to Sequence 6 using a propellar mixer while maintaining the temperature from 85 to 90° C. until the ingredients were dissolved and a milky white solution was obtained. The mixture of Sequences 1 through 4 was added and allowed to mix for 10 minutes with moderate agitation. Sequence 13 was added while maintaining the temperature at 83 to 85° C. and mixing for 5 minutes. Sequences 14, 15, and 17 were added to the mixture and mixed well. The composition was poured into stick molds.

EXAMPLE 2

Cosmetic compositions were made according to the following formulas:

|  | A | B | C | D | E | F | G | H |
|---|---|---|---|---|---|---|---|---|
| PPC[1] | 5.0 | 1.0 | 5.0 | 1.0 | 1.0 | 1.0 | 1.0 | 1.0 |
| PEG-20 methyl glucose sesquiisostearate | — | 3.5 | — | 3.5 | 3.5 | 3.5 | 3.5 | 3.5 |
| Sodium stearate | 6.0 | 8.0 | 6.0 | 8.0 | 8.0 | 8.0 | 8.0 | 8.0 |
| Butylene glycol | 8.0 | 12.0 | 6.0 | 12.0 | 12.0 | 12.0 | 12.0 | 12.0 |
| Water | 45.7 | 41.0 | 37.7 | 50.4 | 40.0 | 40.0 | 44.0 | 45.0 |
| Dimethicone | — | 12.0 | — | 18.0 | 10.0 | 11.0 | 12.0 | 12.0 |
| Isostearyl alcohol | 1.0 | 6.0 | — | 6.0 | 4.0 | 5.0 | 6.0 | 6.0 |
| Preservatives | 1.0 | 1.0 | 1.0 | 1.0 | 1.0 | 1.0 | 1.0 | 1.0 |
| Vitamins | 0.5 | 0.5 | 0.5 | 0.5 | 0.5 | 0.5 | 0.5 | 0.5 |
| Sunscreen | 2.0 | 10.0 | 2.0 | 2.0 | 2.0 | 2.0 | 2.0 | 2.0 |
| Talc | — | — | 3.0 | — | — | 1.0 | — | — |
| Titanium dioxide | — | 5.0 | 8.0 | — | — | 13.0 | — | — |
| Iron oxides | — | — | 3.0 | 0.3 | 9.0 | 2.0 | — | 4.0 |
| Organic pigments | — | — | — | 3.0 | — | — | — | 4.0 |
| Mica | — | — | — | 0.1 | 9.0 | — | 10.0 | 1.0 |
| Black iron oxide | — | — | — | — | — | — | 10.0 | — |
| Magnesium aluminum silicate | 0.8 | — | 0.8 | — | — | — | — | — |
| Sucrose cocoate/sorbitan stearate | 4.0 | — | 4.0 | — | — | — | — | — |
| Vinyl silicone copolymer[2] | 8.0 | — | 6.0 | — | — | — | — | — |
| Isononyl isononanoate | 2.0 | — | 2.0 | — | — | — | — | — |
| Aluminum starch octenylsuccinate | 1.0 | — | 1.0 | — | — | — | — | — |
| Zinc oxide | 2.0 | — | 2.0 | — | — | — | — | — |
| Cyclomethicone | 13.0 | — | 10.0 | — | — | — | — | — |

A = moisturizing stick, B = sunscreen stick, C = foundation makeup, D = blush, E = eyeshadow, F = concealer, G = mascara, H = lipstick.
[1] PPC: the reaction product of casein and carageenan, comprising about 20% by casein and about 80% by weight carageenan
[2] Dimethicone, vinyl dimethicone cross polymer (silicone elastomer)

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A water and oil emulsion solid cosmetic composition for applying color to skin comprising, by weight of the total composition:
   0.1–20% of a carboxylated salt gelling agent,
   0.01–20% of a secondary gelling agent which is a mixture of an aqueous phase gelling agent and an oil phase gelling agent,
   0.1–30% emollient oil,
   0.1–20% surfactant,
   0.1–50% particulates having a particle size of 0.5 to 100 microns, comprised of a mixture of pigments and powders; and
   5–95% water.

2. The composition of claim 1 wherein the water and oil emulsion is an oil-in-water emulsion.

3. The composition of claim 1 wherein the carboxylated salt gelling agent is formed by the reaction of a $C_{12-30}$ fatty acid and a metallic cation.

4. The composition of claim 3 wherein the metallic cation is zinc, aluminum, sodium, calcium, magnesium, or potassium.

5. The composition of claim 4 wherein the fatty acid is a $C_{16-22}$ fatty acid.

6. The composition of claim 5 wherein the fatty acid is stearic acid.

7. The composition of claim 6 wherein the carboxylates salt gelling agent is sodium stearate.

8. The composition of claim 1 wherein the aqueous phase gelling agent, when mixed with water in a 1 to 1 ratio, forms a gel having a gel strength of about 10 to 5,000 grams/cm$^2$ at 25° C.

9. The composition of claim 8 wherein the aqueous phase gelling agent is selected from the group consisting of an anionic polysaccharide, a water soluble protein/polysaccharide complex ("PPC"), and mixtures thereof.

10. The composition of claim 9 wherein the polysaccharide is selected from the group consisting of galactan, galactomannan, glucomannan, polyuronic acid, and mixtures thereof.

11. The composition of claim 10 wherein the polysaccharide is a galactan.

12. The composition of claim 11 wherein the galactan is selected from the group consisting of agar, agarose, kappa carageenan, iota carageenan, lambda carageenan, and mixtures thereof.

13. The composition of claim 9 wherein the aqueous phase gelling agent comprises a PPC.

14. The composition of claim 13 wherein the PPC is the reaction product of at least one protein and at least one polysaccharide.

15. The composition of claim 14 wherein the protein is a natural vegetable or animal protein.

16. The composition of claim 15 wherein the protein is a natural animal protein selected from the group consisting of milk protein, casein, and mixtures thereof.

17. The composition of claim 15 wherein the polysaccharide has a molecular weight ranging from about 500 to 15,000,000 daltons.

18. The composition of claim 17 wherein the polysaccharide contains pendant hydrophilic groups selected from the group consisting of sulfate, pyruvate, phosphate, and mixtures groups.

19. The composition of claim 14 wherein the polysaccharide is a galactan.

20. The composition of claim 1 wherein the emollient oil is a silicone.

21. The composition of claim 1 wherein the oil phase gelling agent selected from the group consisting of a fatty alcohol, synthetic wax, oleaginous material, and mixtures thereof.

* * * * *